United States Patent [19]

De Benneville et al.

[11] 4,009,284
[45] Feb. 22, 1977

[54] GASTROINTESTINALLY ACTIVE THIOUREAS

[75] Inventors: Peter L. De Benneville; Jack N. Moss, both of Philadelphia, Pa.; Esam Z. Dajani, Chicago, Ill.

[73] Assignee: Rohm and Haas Company, Philadelphia, Pa.

[22] Filed: Dec. 3, 1975

[21] Appl. No.: 637,241

Related U.S. Application Data

[60] Division of Ser. No. 553,354, Feb. 26, 1975, Pat. No. 3,950,537, which is a continuation-in-part of Ser. No. 374,852, June 29, 1973, abandoned, which is a division of Ser. No. 175,373, Aug. 26, 1971, abandoned.

[52] U.S. Cl. .............................................. 424/322
[51] Int. Cl.$^2$ ........................................ A61K 31/17
[58] Field of Search ................................... 424/322

[56] References Cited

UNITED STATES PATENTS

| | | | |
|---|---|---|---|
| 3,376,194 | 4/1968 | Berger et al. | 424/322 |
| 3,395,233 | 7/1968 | Duerr et al. | 424/322 |

*Primary Examiner*—Leonard Schenkman
*Attorney, Agent, or Firm*—Terence P. Strobaugh; George W. F. Simmons; Carl A. Castellan

[57] ABSTRACT

Thioureas of the general structure ArylNHC(S)-NR$^1$R$^2$ are useful as antidiarrheal, antimotility or antisecretory agents. Particularly useful are those wherein Aryl is 2-methylphenyl and NR$^1$R$^2$ is NHCH$_2$CH$_2$OH.

6 Claims, No Drawings

GASTROINTESTINALLY ACTIVE THIOUREAS

This application is a divisional application of U.S. Appln. Ser. No. 553,354, filed Feb. 26, 1975, now U.S. Pat. No. 3,950,537 issued Apr. 13, 1976 which was a continuation-in-part of U.S. Appln. Ser. No. 374,852, filed June 29, 1973 now abandoned, which was a divisional application of U.S. Appln. Ser. No. 175,373, filed Aug. 26, 1971, now abandoned.

This invention is concerned with the discovery that certain substituted thioureas have valuable pharmacological properties. Specifically there is provided a new class of structures which have gastrointestinal activity as antimotility, antidiarrheal and antisecretory agents.

Pharmacological studies employing rats and mice as the experimental animals indicate that the instant products and compositions containing the active products are effective antisecretory, antispasmodic or anticholinergic agents which can be used in the treatment of gastrointestinal disorders. When administered in effective therapeutical dosages in conventional vehicles, the instant products are useful in treating gastrointestinal disturbances.

In accordance with the present invention, there is employed an active ingredient having the following formula:

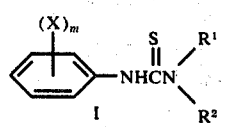

wherein $R^1$ is hydrogen or lower alkyl such as methyl and the like; $R^2$ is lower alkyl such as methyl and the like or a radical of the formula $-CH_2CH_2Y$ wherein Y is amino dimethyl amino or hydroxy; X is lower alkyl such as methyl, ethyl and the like, halo, such as, bromo, chloro and the like or lower alkoxy such as methoxy and the like and m is an integer of 0 to 3.

A preferred embodiment of this invention relates to active products and compositions having as their active ingredients thioureas of the formula:

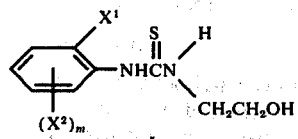

wherein $X^1$ is methyl or ethyl; $X^2$ is methyl, chloro or bromo and m is an integer of 0 to 2.

These thioureas are either known in the art or may be prepared by methods well known to those skilled in the art for example by the addition of a primary or secondary amine, to an aryl isothiocyanate as illustrated by the following formula:

where $R^1$, $R^2$, X and m are as defined above.

Other methods of preparation are reviewed by Schroeder in Chemical Reviews 55, 181 (1955).

Schroeder in Cnem. Reviews 55, 183–189 (1955) discusses the biological properties of thioureas. Specifically discussed are antitubercular, antithyroid, hypnotic, anesthetic, anthelmintic, antibacterial, antiphenoloxidase, insecticidal and rodenticidal properties. Gastrointestinal activity of the type herein described is not mentioned in this survey paper.

The preparation of 1-(2,4-dimethylphenyl)-3-)2-hydroxyethyl)thiourea is given below as a typical method of preparation for these compounds.

The compositions containing the thioureas as the active ingredient and also the thioureas (I) themselves are effective as antimotility, antidiarrheal or antisecretory agents which can be administered in a wide variety of therapeutic dosages in conventional vehicles, for example, oral administration in the form of a tablet or capsules, oral solutions or suspensions or as suppositories. Also, the daily dosage of the product may be varied over a wide range varying from 50 to 2,000 milligrams. The product is preferably administered in subdivided dosages in the form of oral solutions. An effective amount of the drug is ordinarily supplied at a dosage level of from about 0.1 ml. to about 1.0 ml./kg. of body weight. Preferably the range is from about 0.2 ml. to about 0.5 ml./kg. body weight. These dosages are well below the toxic or lethal dose of the products.

Tablets may be prepared by mixing the active ingredient with conventional tabletting ingredients such as calcium phosphate, lactose, corn starch, magnesium stearate and the like. The liquid forms in which the active ingredients may be incorporated include suitable flavored suspending or dispersing agents such as synthetic or natural gums, for example, tragacanth, acacia, methylcellulose and the like. Other dispersing agents which may be employed include glycerin, castor oil and the like. For parenteral administration sterile suspensions and solutions may be desired.

It is also within the scope of this invention to combine two or more of the compounds in this invention in a unit dosage form or to combine one or more of the compounds of this invention with known antimotility, antidiarrheal or antisecretory agents.

The following example is illustrative of how to prepare the compounds of this invention. However, said examples are merely illustrative and should not be construed as limiting the scope of the invention.

1-(2,4-Dimethylphenyl)-3-(2-hydroxyethyl)-thiourea

To 20 g. (0.12 mole) of 2,4-dimethylphenylisothiocyanate in 30 ml. of acetone was added dropwise 10 g. (0.16 mole) of ethanolamine in 20 ml. acetone. The solution was refluxed 1 hour then cooled to 4° C., to give crystals which were filtered off, washed with cold ethanol and dried to afford 1-(2,4-dimethylphenyl)-3-(2-hydroxyethyl)-thiourea, 16.8 g. (54% yield) of white crystals m.p. 137.5°–139° C.

Specific structures which were examined in this study are included in Table I.

Table 1

| | ArylNHC(S)NR$^1$R$^2$ Structures | |
|---|---|---|
| Preparation | Aryl | NR$^1$R$^2$ |
| A | 2-CH$_3$C$_6$H$_4$ | NHCH$_2$CH$_2$OH |
| B | 2-C$_2$H$_5$C$_6$H$_4$ | NHCH$_2$CH$_2$OH |
| C | 2-isoC$_3$H$_7$C$_6$H$_4$ | NHCH$_2$CH$_2$OH |
| D | 4-CH$_3$C$_6$H$_4$ | NHCH$_2$CH$_2$OH |
| E | 2,3-(CH$_3$)$_2$C$_6$H$_3$ | NHCH$_2$CH$_2$OH |

Table 1-continued

| Preparation | Aryl | NR¹R² |
|---|---|---|
| | ArylNHC(S)NR¹R² Structures | |
| F | 2,4-$(CH_3)_2C_6H_3$ | $NHCH_2CH_2OH$ |
| G | 2,5-$(CH_3)_2C_6H_3$ | $NHCH_2CH_2OH$ |
| H | 2,6-$(CH_3)_2C_6H_3$ | $NHCH_2CH_2OH$ |
| I | 3,4-$(CH_3)_2C_6H_3$ | $NHCH_2CH_2OH$ |
| J | 3,5-$(CH_3)_2C_6H_3$ | $NHCH_2CH_2OH$ |
| K | 2-$CH_3$-3-$ClC_6H_3$ | $NHCH_2CH_2OH$ |
| L | 2-$CH_3$-4-$ClC_6H_3$ | $NHCH_2CH_2OH$ |
| M | 2-$CH_3$-5-$ClC_6H_3$ | $NHCH_2CH_2OH$ |
| N | 2-$CH_3$-6-$ClC_6H_3$ | $NHCH_2CH_2OH$ |
| O | 2-$CH_3$-4-$BrC_6H_3$ | $NHCH_2CH_2OH$ |
| P | 2,4-$Cl_2C_6H_3$ | $NHCH_2CH_2OH$ |
| Q | 2-$CH_3$-4-$HOC_6H_3$ | $NHCH_2CH_2OH$ |
| R | 2-$CH_3$-4-$CH_3OC_6H_3$ | $NHCH_2CH_2OH$ |
| S | 2,4,6-$(CH_3)_3C_6H_2$ | $NHCH_2CH_2OH$ |
| T | α-naphthyl | $NHCH_2CH_2OH$ |
| U | β-naphthyl | $NHCH_2CH_2OH$ |
| AA | 2-$CH_3C_6H_4$ | $N(CH_3)_2$ |
| AB | 2,4-$(CH_3)_2C_6H_3$ | $N(CH_3)_2$ |
| AC | 2,6-$(CH_3)_2C_6H_3$ | $N(CH_3)_2$ |
| AD | 2-$CH_3$-4-$ClC_6H_3$ | $N(CH_3)_2$ |
| AE | 2,4-$(CH_3)_2C_6H_3$ | $NHCH_3$ |
| AF | 2,4-$(CH_3)_2C_6H_3$ | $NHC_2H_5$ |
| AG | 2,4-$(CH_3)_2C_6H_3$ | $NHCH_2CH_2NH_2$ |
| AH | 2,4-$(CH_3)_2C_6H_3$ | $NHCH_2CH(CH_3)_2$ |
| AI | 2,6-$(CH_3)_2C_6H_3$ | $NHCH_2CH_2NH_2$ |
| AJ | 2-$CH_3$-4-$ClC_6H_3$ | $NHCH_2CH_2NH_2$ |
| AK | 2,4-$(CH_3)_2C_6H_3$ | $NHCH_2CH_2SH$ |
| AL | 2,4-$(CH_3)_2C_6H_3$ | $N(CH_3) CH_2CH_2OH$ |
| AM | 2,4-$(CH_3)_2C_6H_3$ | $N(CH_2CH_2CH)_2$ |
| AN | 2,4-$(CH_3)_2C_6H_3$ | $NHCH(CH_3)CH_2OH$ |
| AO | 2,4-$(CH_3)_2C_6H_3$ | $NHC(CH_3)_2CH_2OH$ |
| AP | 2,4-$(CH_3)_2C_6H_3$ | $NHCH_2CH(CH_3)OH$ |
| AQ | 2,4-$(CH_3)_2C_6H_3$ | $NHCH_2CH_2CH_2OH$ |
| AR | (2,6-$(CH_3)_2C_6H_3NHC(O)NHCH_2CH_2OH$) | |

The gastrointestinal activity of the compounds of this invention was determined by evaluation in three types of tests, antisecretory, antimotility and antidiarrheal.

Antisecretory

Test procedure of Shay, Komoarov, Fels, Merance, Gruenstein and Spilet in Gastroenterology 5, 43 (1945) and Ishii in Jap. J. Pharmacology 19, 125 (1969). Adult female Wistar rats weighing 140 to 160 g. were starved for 24 hours prior to the test. The animals were anaesthetized with ether, shaved on the abdomen, and a small midline incision made. The pylorus was exposed, ligated, and the wound subsequently closed with wound clips. The animals were treated with the test compound administered either orally one hour prior to pyloric ligation or subcutaneously immediately after ligation. The test compound was administered in distilled water or 0.5% methyl cellulose. Six animals were used for each treatment. Five hours following the ligation, the animals were sacrificed, the stomachs were carefully removed and opened, and the gastric contents measured for volume and titratable acidity. The results are reported in terms of an $ED_{50}$, i.e., the dosage in mg./kg. which caused a 50% reduction in the volume of gastic secretion in the treated rats when compared to the controls. A maximum dosage of 10 mg./kg. was used for the test compounds. A result comparable to the untreated controls was reported as "N", i.e., inactive.

The results are given in Table II.

Table II

| Preparation | $ED_{50}$(mg./kg.) | Preparation | $ED_{50}$(mg./kg.) |
|---|---|---|---|
| | Antisecretory Activity | | |
| A | 3–10 | AA | N |
| B | >10 | AB | N |
| C | N | AC | N |
| D | NT* | AD | N |
| E | 3 | AE | N |
| F | 0.5–1 | AF | N |
| G | N | AG | N |
| H | 0.5–1 | AH | N |
| I | N | AI | N |
| J | >10 | AJ | N |
| K | >10 | AK | N |
| L | 1–3 | AL | >10 |
| M | >10 | AM | N |
| N | N | AN | N |
| O | <10 | AO | N |
| P | N | AP | >10 |
| Q | N | AQ | N |
| R | N | AR | N |
| S | <10 | atropine | 8.0 |
| T | NT | Daricon | 2.4 |
| U | N | Pro-Banthine | 8.0 |

*NT = not tested

The compounds found to be active in the antisecretory test include: 2-$CH_3C_6H_4NHC(S)NHCH_2CH_2OH$; 2,3-$(CH_3)_2$—$C_6H_3)_2C_6H_3NHC(S)NHCH_2CH_2OH$; 2,4-$(CH_3)_2C_6H_3NHC(S)NHCH_2CH_2OH$; 2,6-$(CH_3)_2C_6H_3NHC(S)NHCH_2CH_2OH$; 2-$CH_3$-4-$ClC_6H_3NHC(S)NHCH_2$—$CH_2OH$ and 2,4,6-$(CH_3)_3C_6H_2NHC(S)NHCH_2CH_2OH$.

Antimotility

The method used to measure antimotility is adopted from Janssen and Jageneau, J. Pharmacy and Pharmacology 9, 381 (1957). Adult male mice weighing in the range of 20 to 30 g. were starved for 24 hours prior to the test. The animals were then treated orally with the test compound dissolved in water or suspended in methyl cellulose. One hour later, each animal was dosed with 0.2 ml. of a charcoal suspension consisting of 5% activated charcoal suspended in 0.25% methyl cellulose. The animals were sacrificed 3.5 hours after the charcoal administration and their cecums examined for the presence or absence of charcoal. Under these conditions charcoal appears in the cecum of greater than 90% of placebo-treated animals used as controls. The results are reported in terms of an $ED_{50}$, i.e., the dosage in mg./kg. which prevented the charcoal from entering the cecum in 50% of the treated mice. A maximum dosage of 30 mg./kg. was used. A result comparable to the placebo-treated controls was reported as N, i.e., inactive. The results are given in Table III.

Antidiarrheal

Compounds which were active in the antimotility test were then evaluated in a secondary test which measured a counter-action on diarrhea. This was another type of antimotility test adapted from that reported by Janssen in U.S. Pat. No. 3,539,579. In this test adult male Swiss-Webster mice weighing 30 to 40 g. were employed, using 6 mice per treatment. The test compound was administered orally in a dosage series with a maximum of 30 mg./kg. either in water if soluble or else in 0.5% methyl cellulose. One hour after treatment, each animal received a single dose of 0.3 ml. of castor oil, administered orally. The animals were then individually caged and provided food and water. Three hours thereafter, the presence or absence of diarrhea was noted in all animals. Ninety nine percent of the control animals showed diarrhea. The results are reported in terms of an $ED_{50}$, i.e., the dosage in mg./kg. which inhibited diarrhea in 50% of the treated mice. If there were no changes from the untreated controls, the result was reported as an N, i.e., inactive as an antidiarrheal agent.

The results are included in Table III.

Table III

| Preparation | Antimotility ED$_{50}$(mg./kg.P.O.) | Antidiarrheal ED$_{50}$(mg./kg.P.O.) |
|---|---|---|
| A | 11.5 | 7.8 |
| B | >15 | 15–30 |
| C | N | N |
| D | N | NT* |
| E | 5.0 | 12.5 |
| F | 8.6 | 10.5 |
| G | N | N |
| H | 2.4 | 4.3 |
| I | N | N |
| J | N | NT |
| K | 7.2 | <30 |
| L | 15–30 | <30 |
| M | 7.4 | 15–30 |
| N | <30 | NT |
| O | 18.5 | >30 |
| P | N | N |
| Q | N | N |
| R | 12.5 | 30 |
| S | 6.4 | <30 |
| T | 7.0 | 15–30 |
| U | N | N |
| AA | <30 | <30 |
| AB | 4.4 | 3.8 |
| AC | <30 | NT |
| AD | <30 | NT |
| AE | N | NT |
| AF | N | NT |
| AG | 13 | 10 |
| AH | 20 | N |
| AI | 15.5 | 11.5 |
| AJ | 30 | NT |
| AK | 15–30 | N |
| AL | N | N |
| AM | N | N |
| AN | N | NT |
| AO | <30 | N |
| AP | N | N |
| AQ | N | N |
| AR | N | N |
| atropine | 9.8 | >40 |
| codeine phosphate | 29 | 35 |
| Daricon | 3.4 | 50 |
| Lomotil | 2 | 9.9 |
| morphine sulfate | 9.5 | 14 |
| Pro-Banthine | 14.7 | inactive up to 80 |

NT = not tested

The compounds which were found to be active in the antimotility tests include:

2-$CH_3C_6H_4$NHC(S)NHCH$_2$CH$_2$OH
2-$C_2H_5C_6H_4$NHC(S)NHCH$_2$CH$_2$OH
2,3-$(CH_3)_2C_6H_3$NHC(S)NHCH$_2$CH$_2$OH
2,4-$(CH_3)_2C_6H_3$NHC(S)NHCH$_2$CH$_2$OH
2,6-$(CH_3)_2C_6H_3$NHC(S)NHCH$_2$CH$_2$OH
2-$CH_3$-3-$ClC_6H_3$NHC(S)NHCH$_2$CH$_2$OH
2-$CH_3$-4-$ClC_6H_3$NHC(S)NHCH$_2$CH$_2$OH
2-$CH_3$-5-$ClC_6H_3$NHC(S)NHCH$_2$CH$_2$OH
2-$CH_3$-6-$ClC_6H_3$NHC(S)NHCH$_2$CH$_2$OH
2-$CH_3$-4-$BrC_6H_3$NHC(S)NHCH$_2$CH$_2$OH
2-$CH_3$-4-$CH_3OC_6H_3$NHC(S)NHCH$_2$CH$_2$OH
2,4,6-$(CH_3)_3C_6H_2$NHC(S)NHCH$_2$CH$_2$OH
$\alpha$-naphthylNHC(S)NHCH$_2$CH$_2$OH
2-$CH_3C_6H_4$NHC(S)N(CH$_3$)$_2$
2,4-$(CH_3)_2C_6H_3$NHC(S)N(CH$_3$)$_2$
2,6-$(CH_3)_2C_6H_3$NHC(S)N(CH$_3$)$_2$
2-$CH_3$-4$ClC_6H_3$NHC(S)N(CH$_3$)$_2$
2,4-$(CH_3)_2C_6H_3$NHC(S)NHCH$_2$CH$_2$NH$_2$
2,4-$(CH_3)_2C_6H_3$NHC(S)NHCH$_2$CH$_2$N(CH$_3$)$_2$
2,6-$(CH_3)_2C_6H_3$NHC(S)NHCH$_2$CH$_2$NH$_2$
2-$CH_3$-4-$ClC_6H_3$NHC(S)NHCH$_2$CH$_2$NH$_2$ Certain antisecretory, antispasmodic or anticholinergic agents are commonly used to control hypersecretion and hypermotility which may be associated with gastrointestinal disorders, such as gastritis, peptic ulcer, pylorospasm, and the like. Among these are atropine, codeine phosphate, oxyphencyclimine hydrochloride (Daricon), diphenoxylate hydrochloride (Lomotil), morphine sulfate and propantheline bromide (Pro-Banthine R) which were used as standards in the above antisecretory and antimotility evaluations. It will be noted that many of the thioureas of this invention are more active than these well known standards.

There are various types of diarrhea such as that caused by gastroenteritis, an irritable bowel, functional hypermotility, ulcerative colitis, food poisoning or acute infections. Several antidiarrheal agents now in use include those containing narcotics such as morphine, antibiotics such as neomycin, anticholinergic agents such as oxyphencyclimine hydrochloride (Daricon) or propantheline bromide (Pro-Banthine), bacillus cultures such as *Lactobacillus acidophilus*, clays such as kaolin, and antimicrobials such as furazolidone, and antimotility agents such as diphenoxylate hydrochloride (Lomotil). None of these, however, are based on a thiourea derivative.

The compositions of the invention preferably contain 0.1–90% by weight of a compound of Formula I.

Compositions for oral administration are the preferred compositions of the invention, and these are the known pharmaceutical forms for such administration, such as for example tablets, capsules, syrups and aqueous and oily suspensions. The excipients used in the preparation of these compositions are the pharmaceutically acceptable excipients known in the pharmacist's art.

Preferred compositions are tablets wherein a compound of general Formula I is mixed with an inert diluent such as calcium phosphate in the presence of disintegrating agents, e.g., maize starch, and lubricating agents, e.g., magnesium stearate. Such tablets may, if desired, be provided with enteric coatings by known methods, for example by the use of cellulose acetate phthalate. Similarly capsules, for example hard or soft gelatin capsules, containing a compound of Formula I, with or without other excipients, may be prepared by conventional means and, if desired, provided with enteric coatings in a known manner. The tablets and capsules may conveniently each contain 25–500 mg. of a compound of general Formula I. Other compositions for oral administration include for example aqueous suspensions containing a compound of general Formula I in aqueous media in the presence of a non-toxic suspending agent e.g., sodium carboxymethylcellulose and dispersing agents, and oily suspensions containing a compound of general Formula I in a vegetable oil for example arachis oil.

Compositions of the invention suitable for rectal administration are the known pharmaceutical forms for such administration, such as for example suppositories with cocoa butter or polyethylene glycol bases.

Compositions of the invention suitable for parenteral administration are the known pharmaceutical forms for such administration, for example sterile suspensions in aqueous and oily media or sterile solutions in propylene glycol.

The following examples are submitted by way of illustration but are not to be construed as limiting the invention.

EXAMPLE 1

A blend of 1-(2,6-dimethylphenyl)-3-(2-hydroxyethyl)thiourea (25 parts), corn starch (10 parts), calcium phosphate (20 parts), microcrystalline cellulose (44 parts) and magnesium stearate (1 part) is compressed in a tableting machine in a size to produce a tablet containing 50 mg. of the thiourea.

EXAMPLE 2

A blend of 50 parts of 1-(2-methylphenyl)-3-(2-hydroxyethyl)thiourea, 23 parts of dextrose monohydrate, 23 parts of calcium phosphate and 4 parts of magnesium stearate is packaged into hard gelatine capsules so that each capsule contains 75 mg. of the thiourea.

EXAMPLE 3

A blend of 50 parts of 1-(2-methyl-4-chlorophenyl)-3,3-dimethylthiourea and 50 parts of spray-dried skimmed milk powder is encapsulated in spherical soft gelatine capsules so that each capsule contains 25 mg. of the thiourea.

EXAMPLE 4

Suppositories weighing 1 g. and containing 100 mg. of 1-(2,4-dimethylphenyl)-3-(2-dimethylaminoethyl)-thiourea are prepared in a conventional manner using a base of polyethylene glycol 4000 (33%), polyethylene glycol 6000 (47%) and water (20%).

The dosage requirement to achieve the antisecretory, antimotility or antidiarrheal effect in the mammal will vary with various factors such as the species of animal, general health and tolerance of the animal, weight, sex and age of the animal, the nature and severity of the condition being treated, and the like. Generally a total daily dosage would be in the range of 1 to 25 mg. per kg. of body weight. Advantageously equal doses will be administered from one to six times daily.

Table IV gives the literature references for the known compounds and analytical data for the novel compounds. The structures for the compounds are given in Table I (supra).

These novel and useful thioureas belong to the class of compounds of the general structure

wherein
1. when $R^1$ is hydrogen and $R^2$ is the group $—CH_2CH_2Y$ wherein
   Y is amino, dimethylamino or hydroxy,
   Aryl is
   a. 2-ethylphenyl,
   b. 2,4,6-trimethylphenyl or
   c. the group

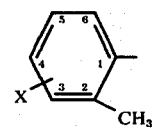

wherein X is 4-bromo, a 4-chloro or 6-chloro group, a 4-methoxy group or a 3-methyl group,
2. when $R^1$ is hydrogen and $R^2$ is the group $—CH_2CH_2Y$ wherein
   Y is amino or dimethylamino,
   Aryl is 2,4-dimethylphenyl, or 2-methyl-4-chlorophenyl or
3. when $R^1$ and $R^2$ are methyl,
   Aryl is 2,6-dimethylphenyl.

What is claimed is:

1. A method for treating a mammal suffering from gastrointestinal disturbances which comprises administering to said mammal in an amount effective to reduce gastric secretions, a compound of the formula:

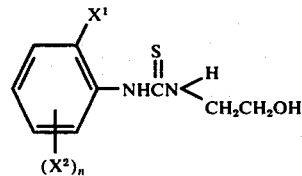

Table IV

Identity of AryINHC(S)NR¹R² Structures

| Preparation | Empirical Formula | Melting Point (° C.) | Literature Reference or Analysis | | | |
|---|---|---|---|---|---|---|
| | | | %C | %H | %N | %S |
| A | | 124 | French patent 1,356,908 | | | |
| B | $C_{11}H_{16}N_2OS$ | 131 | 58.6(58.9) | 7.0(7.1) | 12.4(12.5) | 14.5(14.0) |
| E | $C_{11}H_{16}N_2OS$ | 137 | 58.8 | 7.3 | 12.5 | 14.4 |
| F | | 127 | Maybridge Chemical Co. catalog | | | |
| H | | 129 | French Patent 1,356,908 | | | |
| K | | 140 | French Patent 1,356,908 | | | |
| L | $C_{10}H_{13}ClN_2OS$ | 127 | 49.3(49.2) | 5.5(5.6) | 11.6(11.5) | 13.3(13.1) |
| M | | 135 | Maybridge Chemical Co. catalog | | | |
| N | $C_{10}H_{13}ClN_2OS$ | 95 | 49.5 | 5.2 | 11.5 | 13.1 |
| O | $C_{10}H_{13}BrN_2OS$ | 146 | 41.9(41.5) | 4.7(4.5) | 9.7(9.6) | 11.1(11.1) |
| R | $C_{11}H_{16}N_2O_2S$ | 176 | 54.6(55.0) | 6.7(6.7) | 11.6(11.7) | 13.3(13.3) |
| S | $C_{12}H_{18}N_2OS$ | 132 | 60.7(60.5) | 7.8(7.6) | 11.9(11.8) | |
| T | | 168 | French Patent 1,356,908 | | | |
| AA | | | J. Pharmacool. Exptl. Therap. 168, 229 (1969) | | | |
| AB | | 161 | C.A. 64,1906a (1966) | | | |
| AC | $C_{11}H_{16}N_2S$ | 154 | 63.0(63.4) | 8.0(7.7) | 13.3(13.5) | 15.4(15.4) |
| AD | | 170 | French Patent 1,555,793 | | | |
| AG | $C_{11}H_{17}N_3S$ | 134 | 59.5(59.2) | 7.7(7.6) | 18.7(18.9) | 14.7(14.3) |
| AH | $C_{13}H_{21}N_3S$ | 102 | 62.6(62.1) | 8.6(8.3) | 17.0(16.6) | 12.5(12.7) |
| AI | | 143 | Bull. Soc. Chim. France 1951, 2114–26 | | | |
| AJ | $C_{10}H_{14}ClN_3S$ | 122 | 49.4(49.4) | 5.5(5.8) | 17.3(17.3) | 13.4(13.2) |

*Values are given as Found (calculated)

wherein $X^1$ is methyl or ethyl; $X^2$ is 3,4 or 6-methyl; 3,4 or 5-chloro or bromo and $n$ is an integer of 0–2.

2. A method according to claim 1 wherein the compound is 1-(2-ethylphenyl)-3-(2-hydroxyethyl)thiourea.

3. A method according to claim 1 wherein the compound is 1-(2,3-dimethylphenyl)-3-(2-hydroxyethyl)-thiourea.

4. A method according to claim 1 wherein the compound is 1-(2-methyl-4-chlorophenyl)-3-(2-hydroxyethyl)-thiourea.

5. A method according to claim 1 wherein the compound is 1-(2-methyl-4-bromophenyl)-3-(2-hydroxyethyl)-thiourea.

6. A method according to claim 1 wherein the compound is 1-(2,4,6-trimethylphenyl)-3-(2-hydroxyethyl)-thiourea.

* * * * *